(12) United States Patent
Zhu (10) Patent No.: US 11,936,414 B2
(45) Date of Patent: Mar. 19, 2024

(54) MRI COMMUNICATION DEVICE

(71) Applicant: Aidao Zhu, Zhejiang (CN)

(72) Inventor: Aidao Zhu, Zhejiang (CN)

( * ) Notice: Subject to any disclaimer, the term of this patent is extended or adjusted under 35 U.S.C. 154(b) by 238 days.

(21) Appl. No.: 17/431,935

(22) PCT Filed: Feb. 20, 2020

(86) PCT No.: PCT/CN2020/000034
§ 371 (c)(1),
(2) Date: Aug. 18, 2021

(87) PCT Pub. No.: WO2020/168836
PCT Pub. Date: Aug. 27, 2020

(65) Prior Publication Data
US 2021/0384934 A1 Dec. 9, 2021

(30) Foreign Application Priority Data

Feb. 18, 2019 (CN) .......................... 201910143605.9
Apr. 17, 2019 (CN) .......................... 201910332123.8

(51) Int. Cl.
*H04R 27/00* (2006.01)
*A61B 5/055* (2006.01)
(Continued)

(52) U.S. Cl.
CPC ............. *H04B 1/385* (2013.01); *A61B 5/055* (2013.01); *G01R 33/3692* (2013.01); *H04R 1/10* (2013.01);
(Continued)

(58) Field of Classification Search
CPC ........ H04R 27/00; H04R 1/10; H04R 1/1083; H04R 1/1041; H04R 2227/005
(Continued)

(56) References Cited

U.S. PATENT DOCUMENTS 6,463,316 B1 * 10/2002 Brungart .......... G10K 11/17861
381/72
9,438,981 B2 * 9/2016 Brown ................... H04R 5/033
(Continued)

FOREIGN PATENT DOCUMENTS

CN 101707504 A 5/2010
CN 202353778 U 7/2012
(Continued)

*Primary Examiner* — Disler Paul
(74) *Attorney, Agent, or Firm* — Global IP Services; Tianhua Gu (57) ABSTRACT

The present invention discloses an MRI communication device, which is provided with a control room communication module and a scan room communication module. The scan room communication module includes a receiver, delivering the received first audio signals to the first air tube, while the control room communication module comprises a first sound device, through which the first audio signals are amplified and broadcast. The present invention realizes free bidirectional communication for the control room and the scan room, wherein the receiver can transmit the sound messages to the operator in the control room, making it possible for the technician to manage emergencies of making sounds in the scan room; the air tube is used to transmit audio signals, ensuring the proper operation during MRI exams and preventing them from the influence of the audio signal electromagnetic field from voice calls during MRI scans.

8 Claims, 11 Drawing Sheets

(51) Int. Cl.
    *G01R 33/36*     (2006.01)
    *H04B 1/3827*     (2015.01)
    *H04R 1/10*     (2006.01)

(52) U.S. Cl.
    CPC ..... *H04R 27/00* (2013.01); *H04B 2001/3866* (2013.01)

(58) Field of Classification Search
    USPC ...................................................... 381/74, 77
    See application file for complete search history.

(56) References Cited

U.S. PATENT DOCUMENTS

| | | | | |
|---|---|---|---|---|
| 10,091,574 | B2* | 10/2018 | Smith | H04R 1/2876 |
| 2009/0141924 | A1 | 6/2009 | Her et al. | |
| 2016/0094912 | A1* | 3/2016 | Kropf | G10K 11/22 |
| | | | | 381/334 |

FOREIGN PATENT DOCUMENTS

| | | |
|---|---|---|
| CN | 203563171 U | 4/2014 |
| CN | 204425632 U | 6/2015 |

\* cited by examiner

MRI COMMUNICATION DEVICE

CROSS REFERENCE TO RELATED PATENT APPLICATION

The present application is the US national stage of PCT/CN2020/000034 filed on Feb. 20, 2020, which claims the priorities of the Chinese patent applications No. 201910143605.9 filed on Feb. 18, 2019 and No. 201910332123.8 filed Apr. 17, 2019, which applications are incorporated herein by reference.

FIELD OF THE INVENTION

The present invention relates to the field of medical equipment, particularly to an Mill communication device.

BACKGROUND OF THE INVENTION

With the development of medical technology, the MRI examination and CT examination are essential parts in medical field.

During an Mill exam or a CT exam, the patient is put in the scan room, and the Mill or CT technician is in the control room, operating the equipment to scan the patient. The scan room is completely separated from the control room, which results in the communication problem between the MRI or CT technician and the patient. Though the existing Mill or CT equipment has communication devices disposed in the control room, the one-way communication can only deliver the voice from the control room to the scan room to let the patient act under the technician's instructions, moreover, the speaker the technician in the control room use to give instructions to the patient is arranged high, plus the influence of Mill noise of high intensity, which result in muffled voice. In addition, the patient in the scan room can't speak to the technician in the control room, which makes the technician has no way of knowing whether there are emergencies or discomfort happened to the patient or not so that the technician can't act accordingly, thus the misdiagnosis of Mill exams or CT exams may arise, reducing the accuracy and reliability of MRI exams or CT exams.

SUMMARY OF THE INVENTION

Given the above-mentioned, an object of the present invention is to provide an MRI communication device in order to realize the bidirectional communication for the technicians in control room and the patients in scan room during Mill examinations.

The present invention provides an Mill communication device having a control room communication module and a scan room communication module.

The scan room communication module includes a receiver, delivering the received first audio signals to the first air tube.

The control room communication module comprises a first sound device, through which the first audio signals are amplified and broadcast.

Further, the control room communication module comprises a second sound device; the scan room communication module further consists of an earphone, wherein the second audio signals generated by the second sound device are transmitted to the second air tube, and then picked up by the earphone for broadcasting.

Even further, the first sound device comprises an amplifier, a microphone, a first amplifier and a first speaker. The amplifier includes a big end and a small end, wherein the microphone is located at the big end, and the first air tube is connected to the small end. The first speaker, the first amplifier and the microphone are sequentially connected via wires.

The second sound device consists of a microphone, a second amplifier, a second speaker and a first acoustic wave concentrator, wherein the first acoustic wave concentrator has a big end and a small end. The microphone, the second amplifier and the second speaker are successively connected via wires. The second speaker is disposed at the big end of the acoustic wave concentrator, of which the small end is linked to the second air tube.

Further, the earphone includes a left-ear cover, a right-ear cover and a tee connector. A left-ear voice output port and a right-ear voice output port are respectively arranged in the left-ear cover and the right-ear cover; the tee connector comprises an input port, a first output port and a second output port. The left-ear voice output port and the right-ear voice output port respectively passes through the left-ear air tube and the right-ear air tube and connects with the first output port and the second output port of the tee connector, the input port therein is linked to the second air tube.

Even further, the receiver consists of a sound collector, a second acoustic wave concentrator, a transmission arm and a cross connector, wherein the second acoustic wave concentrator has a big end and a small end; the cross connector, including a first interface and a second interface, is disposed in the left-ear cover; the sound collector has a diaphragm configured thereon. The diaphragm is located at the big end of the second acoustic wave concentrator, and the small end, via the third air tube, joins to the first interface of the cross connector, the second interface therein is linked to the first air tube. The third air tube is disposed in the transmission arm.

Further, a switching device is installed between the control room communication module and the scan room communication module.

The first air tube has a first portion and a second portion, wherein the first portion is connected to the first sound device and the switching device, and the second portion joins to the switching device and the receiver.

The second air tube includes a first portion and a second portion, wherein the first portion is linked to the first sound device and the switching device, and the second portion is connected to the switching device and the earphone.

Further, the switching device has a first switching part and a second switching part used to the plug-in through connection between the first portion and the second portion of the first air tube and/or between the first portion and the second portion of the second air tube.

Even further, the first switching part includes a first hole core and a second hole core, while the second switching part consists of a first jack and a second jack.

The first portion of the first air tube and the second air tube are respectively connected to the first hole core and the second hole core, and the second portion of the first air tube and the second air tube join to the first jack and the second jack respectively.

When the first switching part is connected to the second switching part, the first hole core and the second hole core through-connect with the first jack and the second jack respectively.

Further, the longer the first air tube or the second air tube is, the larger the diameter is.

Further, the control room communication module and the scan room communication module are respectively disposed in the control room and the scan room of the MRI exams. The control room and the scan room are separated by a shield wall, which has holes formed thereon to provide a passageway to the first air tube and the second air tube.

A shielding device is arranged around the holes. The shielding device has a first flange connection part and a second flange connection part joined together by screws. A mating groove having an electromagnetic shielding layer incorporated therein is disposed at one section of the second flange connection part facing the first flange connection part. The first flange connection part and the second flange connection part share a centre hole and a cylinder in same sizes respectively, and the cylinders are sheathed with air tubes. The apertures of the centre holes are identical to the inner diameters of the air tubes.

Even further, the control room communication module further includes a filtering device having a first channel and a second channel. The second speaker connects with the second amplifier via the first channel of the filtering device, and the microphone joins to the first amplifier through the second channel of the filtering device.

The present invention provides an MRI communication device, wherein the first audio signals emitted by the receiver are transmitted to the first sound device and broadcast via the first air tube; the second audio signals sent out by the second sound device are delivered to the earphone and broadcast through the second air tube, which realizes free bidirectional communication for the control room and the scan room. The patient in the scan room can transmit sound messages to the technician in the control room, making it possible for the technician to manage emergencies of making sounds in the scan room. The patient can also receive the technician's messages in the control room by wearing an earphone, making the process of transmission of messages more precise and clearer. Furthermore, the air tube is used to transmit audio signals, ensuring the proper operation during MRI exams and preventing them from the influence of the audio signal electromagnetic field from voice calls during MRI scans.

DETAIL DESCRIPTION OF THE PREFERRED EMBODIMENTS

In the following detailed description of the present invention, reference is made to the accompanying drawings and embodiments which form parts hereof. It is to be understood that the embodiments disclosed herein are only used for purposes of illustration and are in no way limiting. In addition, it is notable that for the sake of description, only the parts, instead of the whole structure, related to the present invention are shown herein.

Before more detailed discussion about the exemplary embodiments, it is to be noted that some exemplary embodiments are described as flowcharts or earphones. Although steps are described as sequential processing in flowcharts, many steps therein can be implemented parallel, concurrently or simultaneously. In addition, the sequence of the steps can be rearranged. It can be ended when the processing is finished, but it is provided with additional steps not included in the attached drawings as well. The processing can be applied to earphones, functions, regulations, subroutines and subprograms, etc.

Moreover, terminologies such as "the first," "the second," etc., are used herein to describe orientations, actions, steps and elements and so on, but in no way limiting. The terminologies herein are only used for purpose of distinction between one orientation, action, step or element and the other. Without departing from the scope of the present invention, for example, the first air tube can be called as the second air tube, and vice verse. The first air tube and the second air tube are both air tubes ostensibly, but are not in the same type essentially. The terminologies such as "the first," "the second," etc. cannot be understood as indication or implication of relative importance or the number of technical features. Thus, the features limited by "the first," "the second," can implicit or explicit one or more features. In the description of the present invention, "multiple," "a plurality of" refer to "at least two", unless there are other clear and specific limitations.

Embodiment 1

A non-magnetic dual channel communication device and shielding-layer air tube microphone are characterized by the installation of a receiving and sending device in the control room.

The disposed special microphone has wires connected to the amplifying circuit in the circuit board to amplify signals and then is linked to one end of the speaker via wires, and the other end of the speaker is arranged at the big end of the acoustic wave concentrator, wherein the small end joins to one end of the air tube, the other end of the air tube is connected to a core hole in a socket. An active connection is set up to link the socket to the plug of the air tube earphone. One hole of the plug is connected to one end of an air tube, and the other end of the air tube is linked to the input port of a tee having two output ports connected to one ends of one air tube respectively, wherein the other ends of the two air tubes join to the voice output ports which are respectively disposed in the two ear covers for ears to pick up voice.

Embodiment 2

An air tube earphone as claimed in embodiment 1 is provided with a receiver (4D) having a diaphragm arranged thereon. The diaphragm is installed at the big end of the acoustic wave concentrator, wherein the small end is connected to one end of the air tube. The air tube is incorporated in an adjustable plastic transmission arm (25D) that can be easily bent. The other end of the air tube is linked to a port of a cross (2D) in the ear cover, and the connecting other port of the cross (2D2) is joined to one end of the air tube (26D), and the other end of the air tube (26D) is connected to the other hole in the plug of the air tube earphone. The plug of the air tube earphone and the socket cooperatively formed active connection therebetween.

The other core having a hole in the plug is connected to the air tube, and the end of the air tube is linked to the small end of the small amplifier (14D), wherein the big end is provided with a microphone (14D1), the wire of the microphone (14D2) leads to the amplifier (16D) of circuits, through which the signals are amplified and delivered to the speaker (17D), conveying the patient's speech in the scan room to the technician in the control room. The two air tubes (12D),(13D) are arranged parallel outside the speaker housing (17D) and lead to the socket (11D). The length of the two parallel air tubes is determined by the distance between the scan room and the control room.

A hard tube (48D1) is disposed at one side of the tee.

Embodiment 3

The transmission arm (25D) according to embodiment 2 is made of 316L stainless steel. The hard tubes (48D1) are combined to the tee (48D), converting the tee (48D) into a bottom. The increased two-way lines replace the hard tube. Other arrangements are the same as that in embodiment 2.

Embodiment 4

The bottom made up of the tee and hard tubes as claimed in embodiment 3 is arranged as an overall bottom sheathed in a Hafu cover (7D) to increase firmness and beauty. Other arrangements are as same as that in embodiment 2.

Embodiment 5

The audio signals from the special microphone (42D) in the control machine are delivered to the amplifying circuit (44D) on the circuit board via a wire (41D) for amplifying signals. The amplified audio signals, passing through the metal-shielded audio wire, are transmitted to one of the passageways in the filter (37D), filtering electric waves affecting the frequency sweeping room and then through an audio signal line (33D-1), arrive to the speaker (29D). The speaker (31D) is positioned at the big end of the acoustic wave concentrator (28D), of which the small end is connected to a corresponding core through-hole in the jack (27D) of the socket (26D) via an air tube.

The other core through-hole in the jack (27D) is linked to the small end of the amplifier (30D) via a soft tube (32D), wherein the big end is provided with a microphone (31D); the microphone (31D) joins to the other passageway of the filter (37D) via an audio wire (33D). After passing through the filter (37D), the microphone is linked to the amplifier (45D) on the circuit board through an audio wire to amplify signals, after which the amplified audio signals are delivered to the speaker (46D) for technicians in the control room to pick up the voice.

The filter (37D) is dedicated only for the scan room of an MRI scan or a CT scan.

Embodiment 6

Fiber optic cables are adopted in the present embodiment to form the audio signal line. Other installations are the same as that in embodiment 5.

Embodiment 7

In the present embodiment, a piezoelectric ceramic speaker is adopted in the scan room, and a moving-coil speaker is used in the control room.

Embodiment 8

Figure 7:
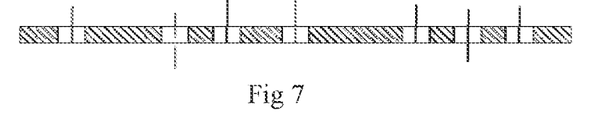
FIG. 7 and FIG. 8 are schematic views of the shape of the shielding layer.
Figure 8:
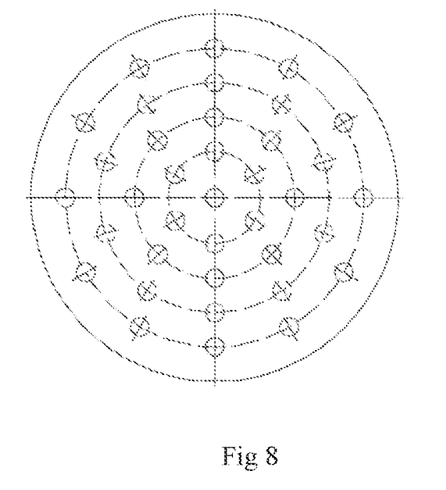
Figure 11:
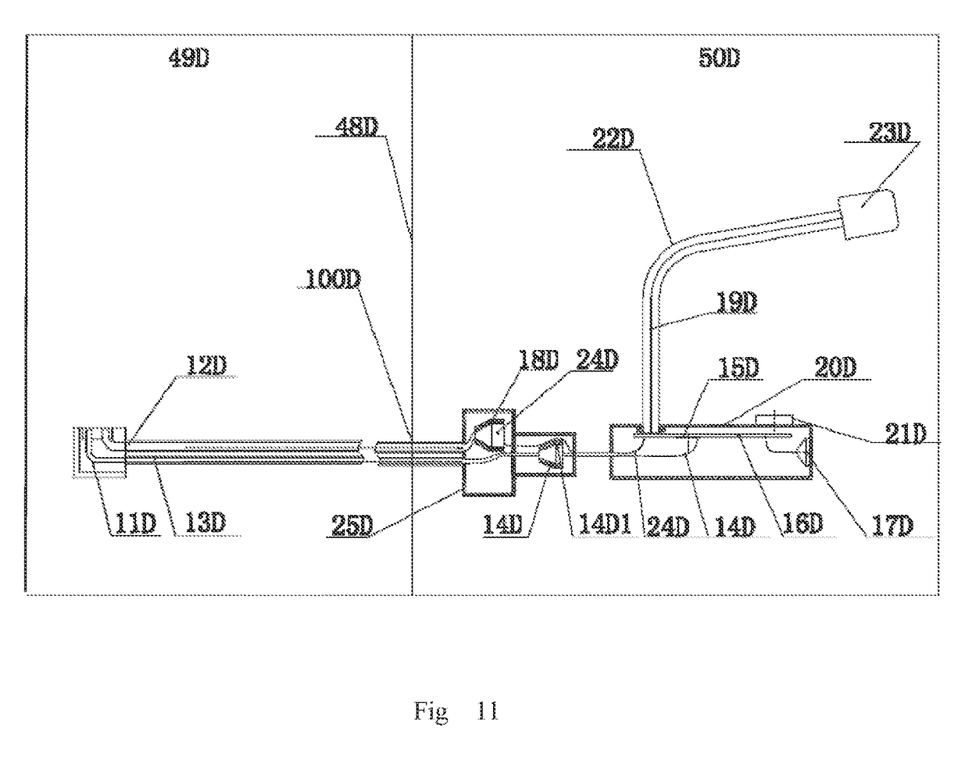
FIG. 11 is a schematic view of the mounting position of the shielding device.

A shielding device is disposed on the shield wall (48D) or the vertical surface (100D in FIG. 11) of the air tube positioned between the acoustic wave concentrator and the small microphone of the air tube microphone. A cone connector (103D) is located at one end of the shielding device; through-holes are arranged at the conical end of the connector (103D). The aperture of the through-holes is identical with the inner diameter of the air tubes. A cylindrical hole a bit larger than the air tube in inner diameter is disposed at the other end of the connector, wherein the cylindrical hole has a shielding layer (102D) carrying a plurality of evenly distributed holes on its surface formed therein. The aggregate sectional area of the holes equals the inner sectional area of the air tube as shown in FIG. 7 and FIG. 8. The shielding layer mounting hole and the inner hole at the conical end are connected by a taper hole to form a horn mouth.

Figure 5:
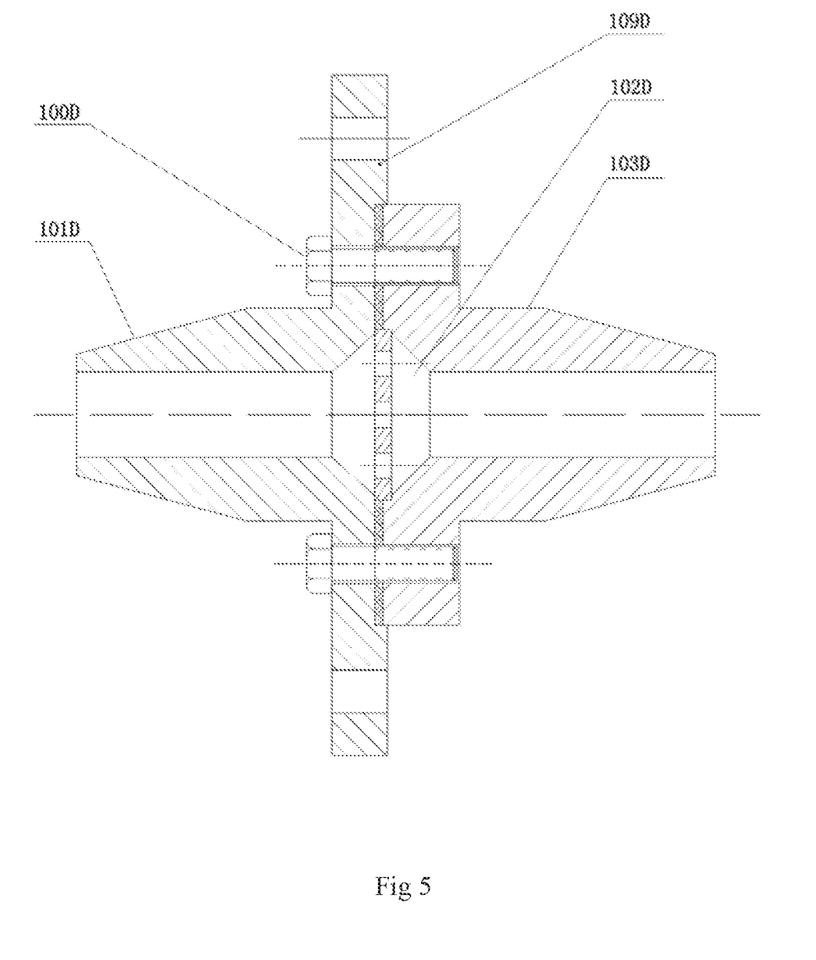
FIG. 5 and FIG. 6 are schematic views of the structure of the shielding device of the air tube microphone.
Figure 6:
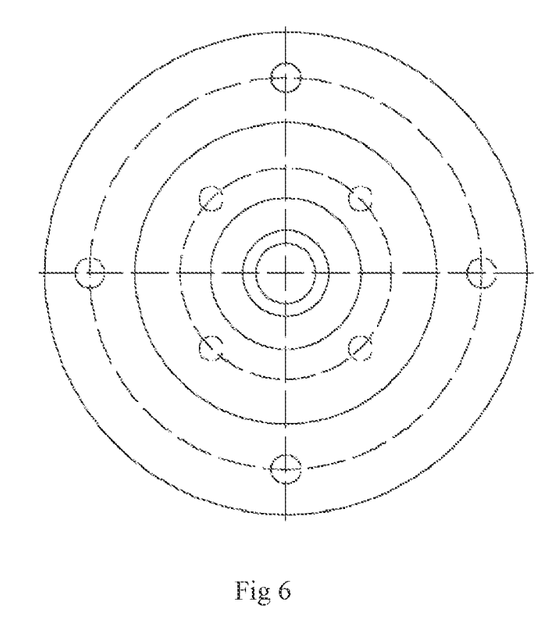

A flange connector (101D) is arranged at the big end of the cone connector (103D); the flange of the flange connector (101D) is connected to the cone connector (103D) via screws (108D). The cone connector (103D) and the flange connector (101D) have a rubber mat incorporated therebetween for seal. The inner hole and the taper horn mouth of the inner hole of the flange connector (101D) and the ones of the cone connector are arranged symmetrically. The cone connector (103D), the flange connector (101D) and the shielding layer (102D) form the shielding device of the air tube microphone. As shown in FIG. 5 and FIG. 6, both ends of the shielding device are sheathed with air tubes, forming an air tube microphone having a shielding device.

The shielding device can separate active microphones, circuits and elements from the passive parts of the air tube microphone, achieving an effect of noninterference of each other and good transmission of sound waves.

Embodiment 9

In the present embodiment, a shielding device of an air tube is configured at the 100D of the speaker air tube (12D). The structure of the shielding device is as same as the one in claim 5. According to FIG. 5 and FIG. 6, the sound port of 24D in the speaker is connected to the cone connector (103D1); the socket part of the air tube joins to the flange connector (101D1), forming a shielding device of the speaker air tube, which isolates the speaker and prevents its circuits from disturbing all the devices in the separation plate.

Embodiment 10

Figure 9:
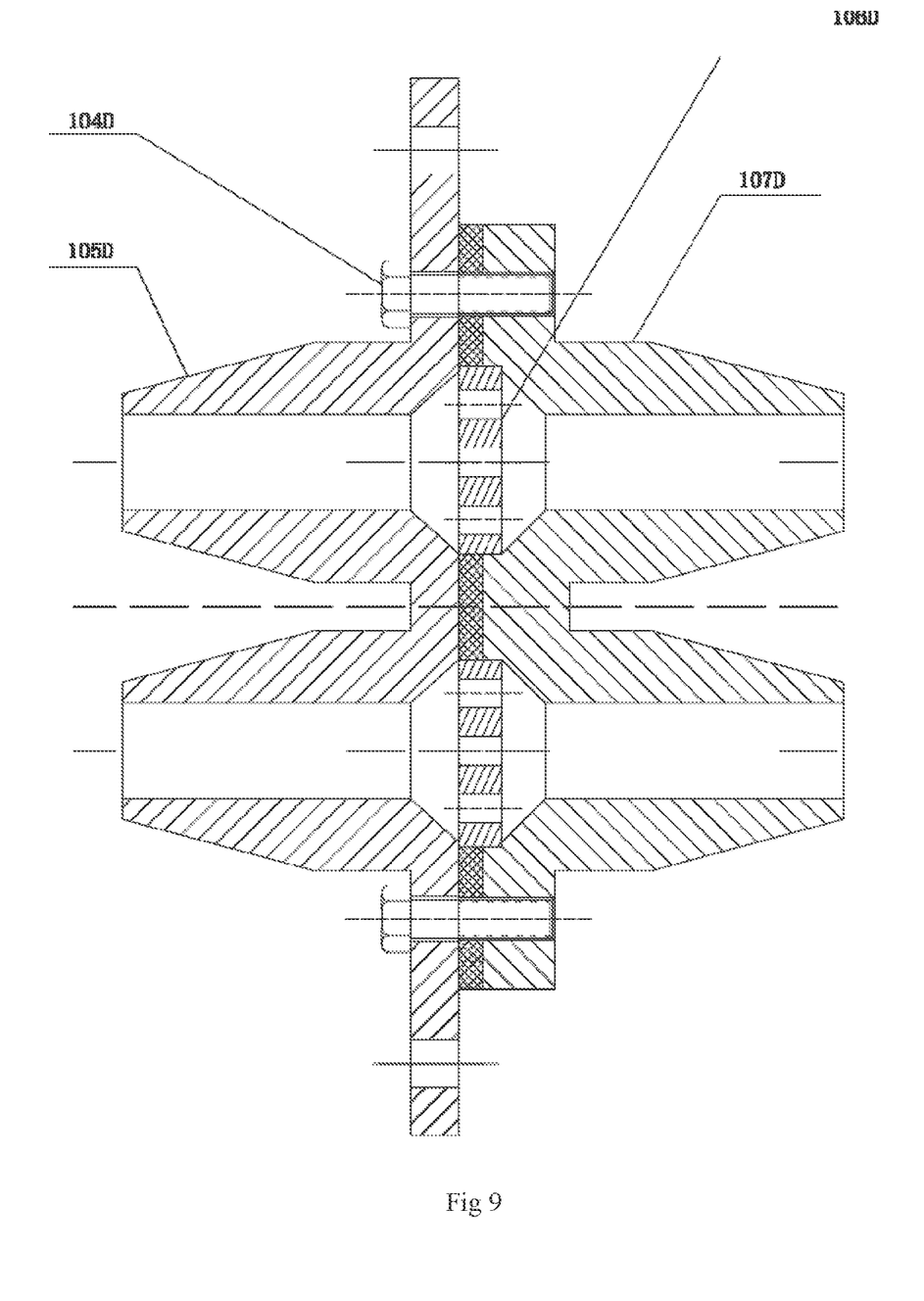
FIG. 9 and FIG. 10 are schematic views of the shielding device having the speaker (24D) and the shielding device of the air tube microphone joined together thereon.
Figure 10:
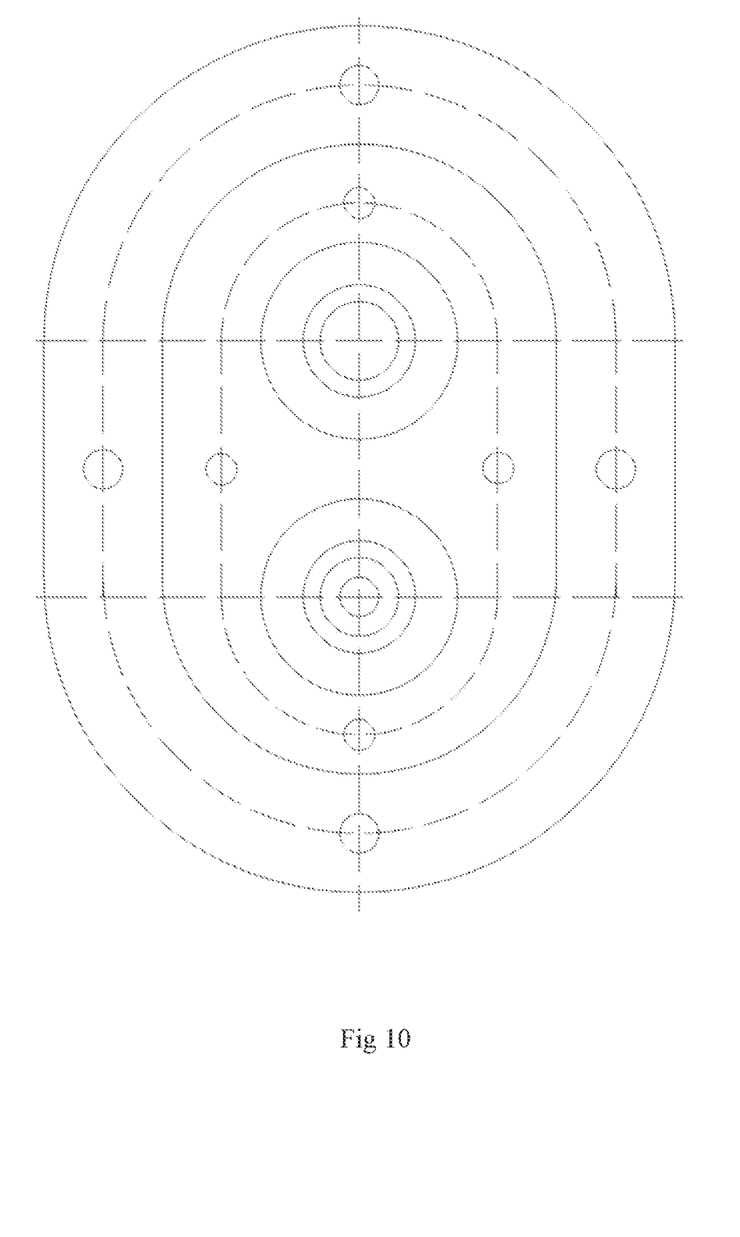

In the present embodiment, the air tube shielding device of the air tube microphone and the one of the speaker are installed together as one. The flange is oval as shown in FIG. 9 and FIG. 10.

Embodiment 11

In the present embodiment, all materials for the shielding device are identical with the materials for the original shielding layer of the MRI communication device.

Embodiment 12

Figure 12:
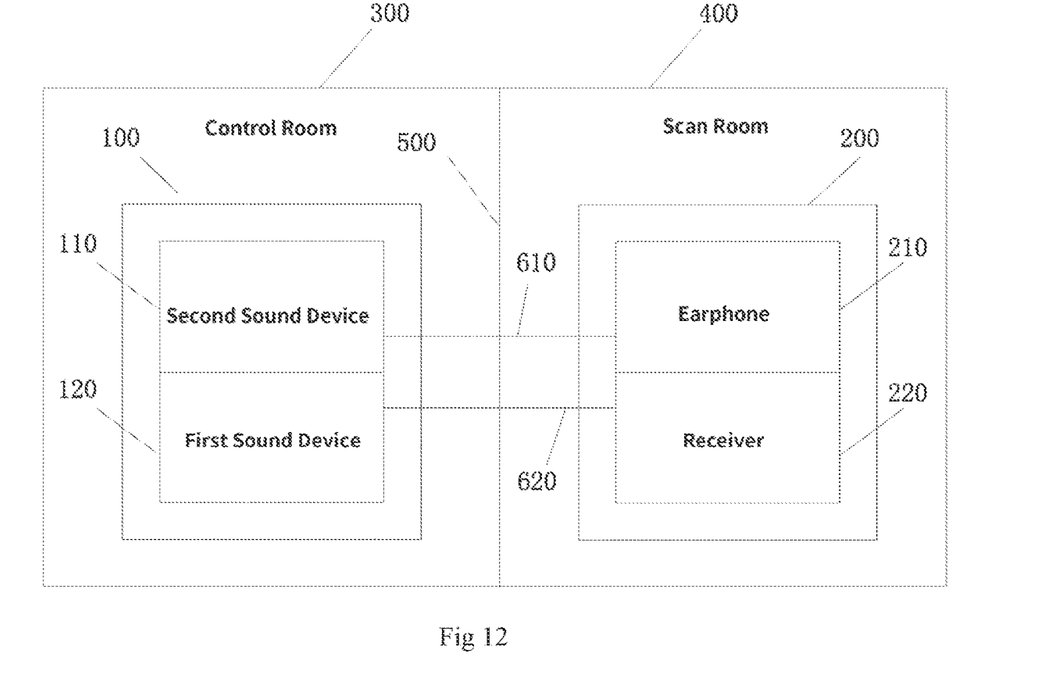
FIG. 12 is a schematic view of the structure of an MRI communication device provided for the embodiment 12 in the present invention.

FIG. 12 is a schematic view of the structure of an MRI communication device provided for the embodiment 12 in the present invention. The present invention can be applied to the scene operating an MRI exam. According to FIG. 12, the MIll communication device comprises a control room communication module (100) and a scan room communication module (200). It should be noted that the MIll communication device further includes a scanner, a scanning bed, a control panel and other working modules. No limitations are made to the structures of the modules and working principles.

The control room communication module (100) and scan room communication module (200) are respectively disposed in the control room (300) and scan room (400) which have a shield wall (500) formed therebetween for separation. The control room communication module (100) comprises a first sound device (120) and a second sound device (110); the scan room communication module (200) includes an earphone (210) and a receiver (220). The second sound device (110) and the earphone (210) are connected via the second air tube (610), and the first sound device (120) is linked to the receiver (220) through the first air tube (620).

The working process of the embodiments in the present invention is as follows: when the patient in the scan room (400) have emergencies to inform the technician in the control room (300), the patient send out first sound messages through the receiver (220). The receiver (220) transforms the first sound messages into first audio signals and input the signals to the first air tube (620) which further conveys the signals to the first sound device (120). The first sound device (120) amplifies and restores the first audio signals and then transforms them into the patient's first sound messages so that the technician in the control room (300) can pick up the first sound messages.

When the technician in the control room (300) gives instructions or information to the patient in the scan room (400), the patient in the control room (300) send out second sound messages to the second sound device (110) which will transform the messages into second audio signals and input them into the second air tube (610) and the second air tube (610) continues to deliver the first sound signals to the earphone (210) to amplify and restore the signals so that the second audio signals can be converted into the technician's second sound messages and the patient in the scan room (400) can pick up the messages with an earphone near his/her face.

Further, the longer the air tube (all air tubes referred to in the present embodiments) is, the father the audio signals travel in the air tube. The diameter of the air tube should be made larger in order to reduce the loss of audio signals.

The present invention provides an MRI communication device, wherein the first audio signals emitted by the receiver are transmitted to the first sound device and broadcast via the first air tube; the second audio signals sent out by the second sound device are delivered to the earphone and broadcast through the second air tube, which realizes free bidirectional communication for the control room and the scan room. The patient in the scan room can transmit sound messages to the technician in the control room, making it possible for the technician to manage emergencies of making sounds in the scan room. The patient can also receive the technician's messages in the control room by wearing an earphone, making the transmission of messages more precise and clearer. Furthermore, the air tube is used to transmit audio signals, ensuring the proper operation during MIll exams and preventing them from the influence of the audio signal electromagnetic field from voice calls during MRI scans.

Embodiment 13

Figure 13:
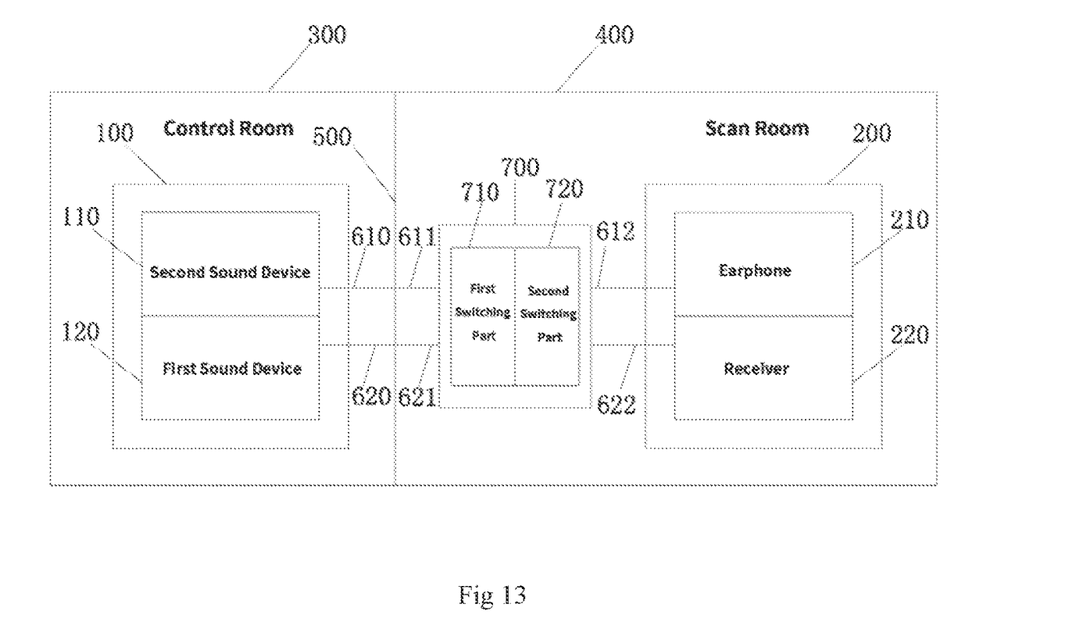
FIG. 13 is a schematic view of the structure of an MRI communication device provided for the embodiment 13 in the present invention.

FIG. 13 is a schematic view of the structure of an MRI communication device provided for the present embodiment which is a further optimization of the above ones. According to FIG. 13, based on the above embodiments, the MIll communication device has a switching device installed between the control room communication module (100) and the scan room communication module (200), because of which the first air tube (620) has a first portion (621) and a second portion (622), and the second air tube (610) also has a first portion (611) and a second portion (612), wherein the first portion (611) of the second air tube is linked to the second sound device (110) and the switching device, and the second portion (612) of the second air tube is connected to the switching device (700) and the earphone (210); the first portion (621) of the first air tube is connected to the first sound device (120) and the switching device (700), and the second portion (622) of the first air tube joins to the switching device (700) and the receiver (220).

Further, the switching device (700) has a first switching part (710) and a second switching part (720) and a plug-in connection is adopted therebetween. For example, setting the first switching part (710) as a socket and the second switching part (720) as a plug. When the first switching part (710) and the second switching part (720) are linked, a through-connection can be made between the first portion (611) and the second portion (612) of the second air tube (610), and between the first portion (621) and the second portion (622) of the first air tube (620).

In the present invention, the installation of the switching device between the control room communication module and the scan room communication module makes both modules independent. The connection between the control room communication module and the scan room communication module can be controlled via the switching device, improving the utilization convenience of both modules.

Embodiment 14

Figure 14:
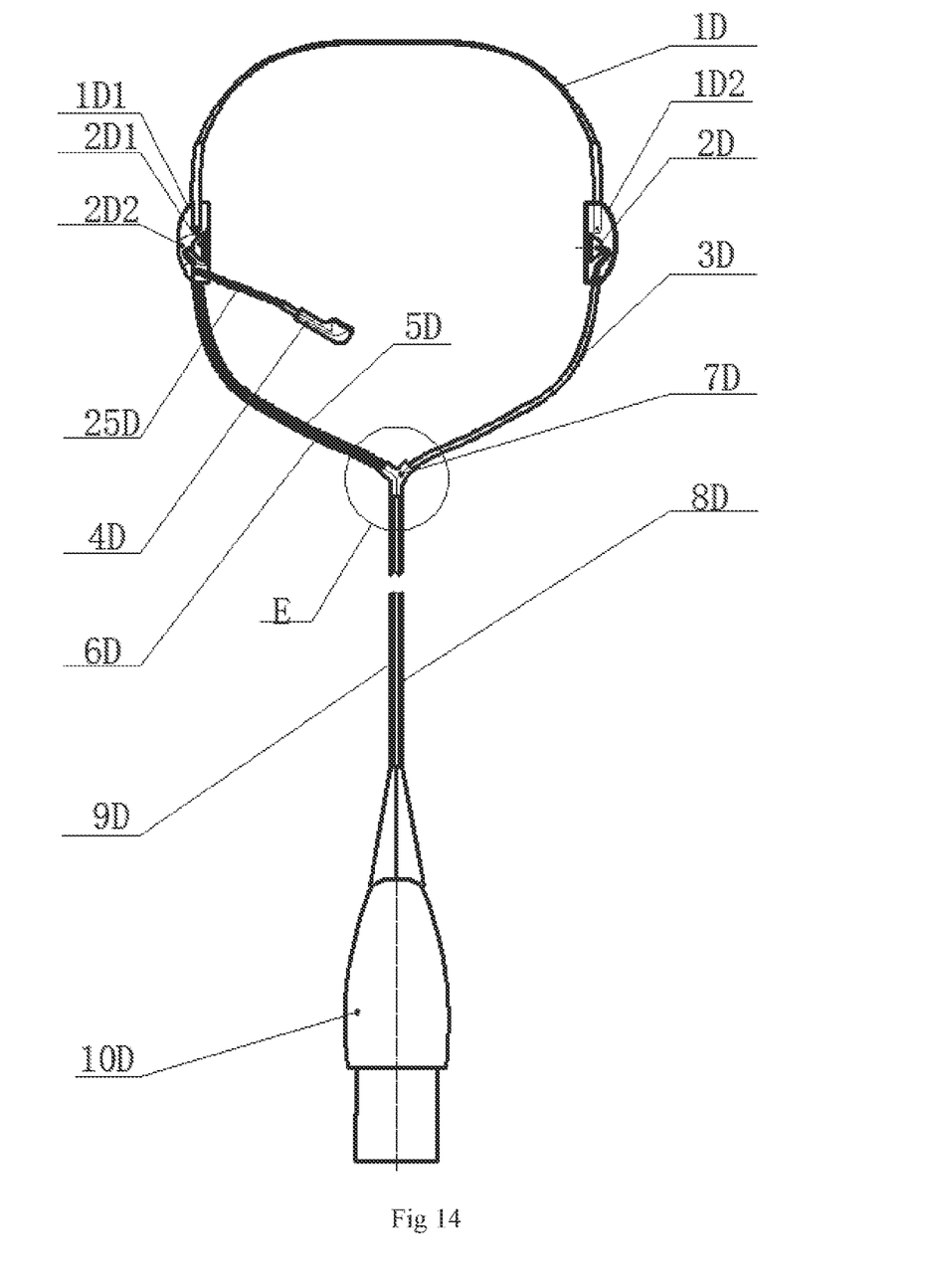
FIG. 14 is a schematic view of the structure of a scan room communication module provided for the embodiment 14 in the present invention.

FIG. 14 is a schematic view of the structure of a scan room communication module provided for the present embodiment which is a refinement of the above embodiments. As shown in FIG. 14, the scan room communication module includes a left-ear cover (1D1), a right-ear cover (1D2), a tee connector (48D), a sound collector (4D) a second acoustic wave concentrator, a transmission arm (25D), a cross connector (2D2) and a plug (10D), wherein a left-ear voice output port (2D1) and right-ear voice output port (2D) are respectively disposed in the left-ear cover (1D1) and right-ear cover (1D2). The tee connector including an input port, a first and a second output port as shown in FIG. 10 is sheathed in a Hafu cover (7D) and has a hard tube (48D1) arranged at one side thereon. The left-ear voice output port (2D1) and the right-ear voice output port (2D) are respectively connected to the first output port and the second output port of the tee connector (48D) through left-ear air tube (5D) and right-ear air tube (3D). The input port of the tee connector (48D) is linked to the second air tube (8D) which joins to the second jack of the plug (10D).

The second air tube (8D) in the scan room communication module links with the second air tube in the control room communication module via the second jack of the plug (10D) to receive the second audio signals from the control room and then respectively deliver them to the left-ear air tube (5D) and right-ear air tube (3D) which transmit the second audio signals respectively to the left-ear voice output port (2D1) and right-ear voice output port (2D). Users can pick up the second sound messages sent from the control room communication module by wearing the left-ear cover (1D1) and right-ear cover (1D2).

The second acoustic wave concentrator comprises a big end and a small end. The cross connector (2D2) including a first port and a second port is disposed in the left-ear cover (1D1). The sound collector (4D) has a diaphragm incorporated thereon; the diaphragm is positioned at the big end of the acoustic wave concentrator, and the small end joins to the first port of the cross connector (2D2) via third air tube; the second port of the cross connector (2D2) is linked to the first air tube which is positioned in the scan room communication module having a top half and a bottom half, wherein the top half (6D) parallel to the left-ear air tube (5D) is in between the second port of the cross connector (2D2) and the tee connector (48D); the bottom half parallel to the second air tube (8D) is the part between the tee connector (48D) and the first jack of the plug (10D). The third air tube is disposed in the transmission arm (25D) and the second acoustic wave concentrator is arranged in the housing of the sound collector (25D) which are not labeled in the figure.

The sound collector (4D) transforms the first sound messages sent by the patient in the scan room to first audio signals and transmits them to the first air tube through the third air tube, and the first sound messages will be picked up by the control room communication module and then by the technician in the control room.

Embodiment 15

The present embodiment provides the schematic view of the structure of a control room communication module as in the reference diagram 2. The present embodiment is a further detailed description of the control room communication module. According to FIG. 2, the control room communication module consists of a megaphone (23D), a second amplifier (15D), a second speaker (24D), a first acoustic wave concentrator (18D), an amplifier (14D), a microphone (14D1), a first amplifier (16D) and a first speaker (17D). The present embodiment can set or cancel the amplifier (14D). The first acoustic wave concentrator (18D) has a big end and a small end; the megaphone (23D), the second amplifier (15D) and the second speaker (24D) are sequentially connected through wires; the second speaker (24D) is installed at the big end of the first acoustic wave concentrator (18D) and the small end is linked to the second air tube (12D) which joins to the second hole core of the socket (11D).

Figure 1:
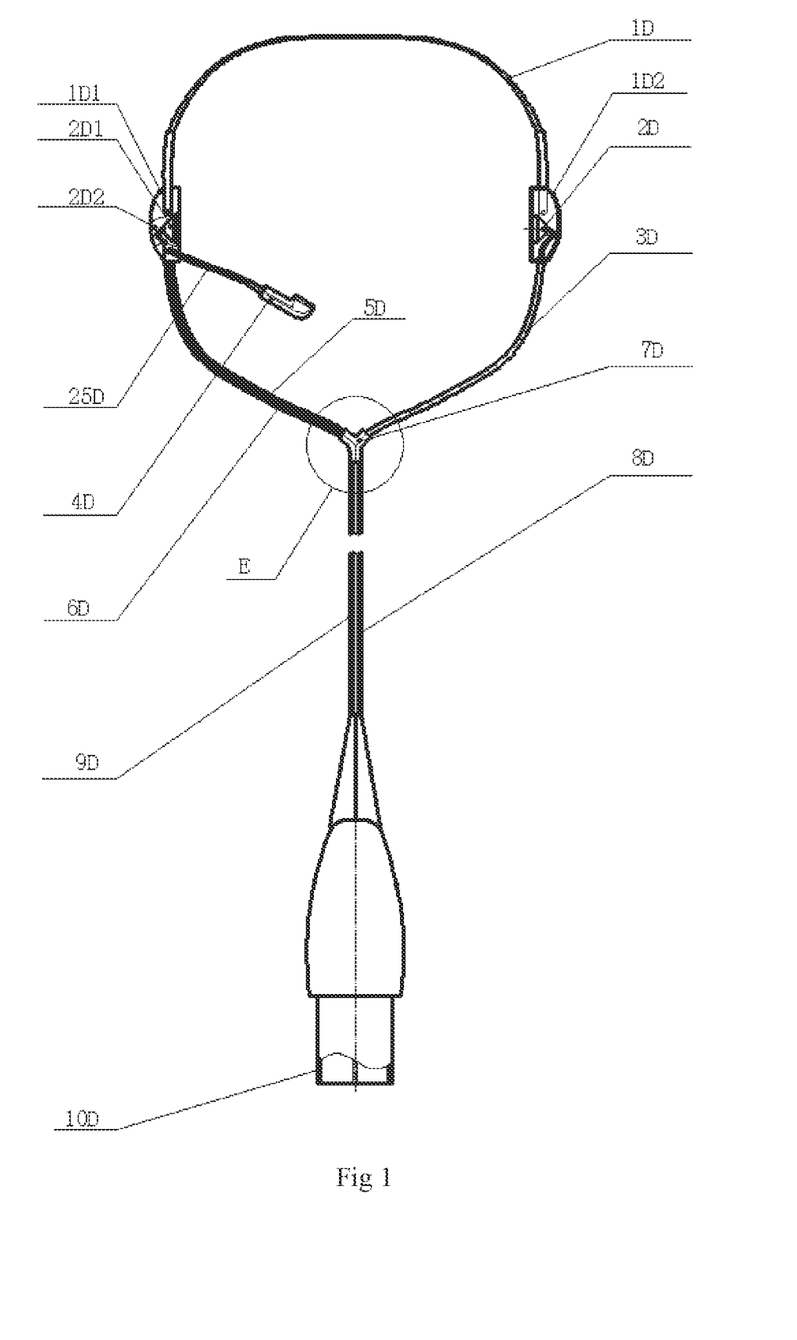
FIG. 1 is a schematic view of the structure of the dual-channel communication all-air tube earphone.
Figure 2:
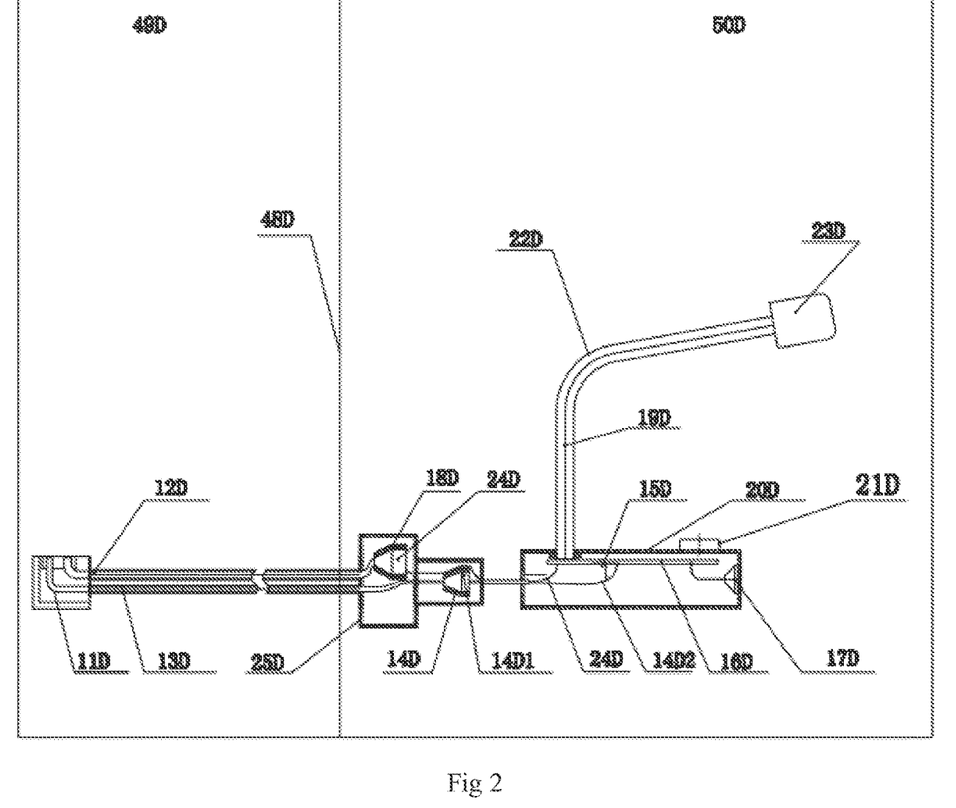
FIG. 2 is a schematic view of the process of speaking and listening, the amplification of voices and the access of the all-air tubes to the scan room (49D) and the control room (50D).
Figure 3:
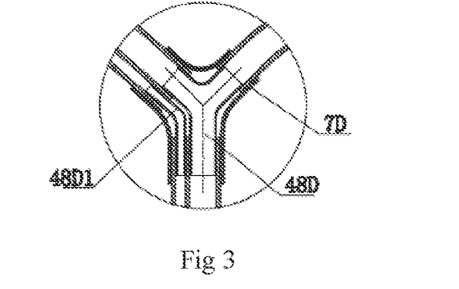
FIG. 3 is a schematic view of the structure inside and outside of the bottom in the all-air tube earphone.

The megaphone (23D) converts the first sound messages emitted by the technician in the control room (50D) into second audio signals and delivers them to the second air tube (12D)(the first portion of the second air tube) in the control room (50D) communication module. The second hole core of the socket (11D) and the second jack of the plug (10D) can be plug-in through connected to the second air tube (12D) (the second portion of the second air tube) in the control room (50D) communication module and the second air tube (8D) in the scan room (49D) communication module so that the second audio signals can be received by the second air tube (8D) in the scan room (49D) communication module and then by the patient in the scan room (49D).

The amplifier includes a big end and a small end, wherein the microphone (14D1) is disposed at the big end; the first speaker (17D), the first amplifier (16D) and microphone (14D1) are sequentially connected through wires; the small end of the amplifier (14D) links to the first air tube (13D) which joins to the first hole core of the socket (11D).

The plug-in through connection between the first hole core of the socket (11D) and the first jack of the plug (10D) enables the first air tube (13D)(the first portion of the first air tube) in the control room (50D) communication module to through-connect with the bottom half (9D) of the first air tube (the second portion of the first air tube) in the scan room (49D) communication module so that the first air tube (13D) in the control room (50D) can receive the first audio signals from the scan room (49D) communication module, and eventually the corresponding first sound messages can be broadcast to the technician in the control room (50D).

Embodiment 16

Figure 15:
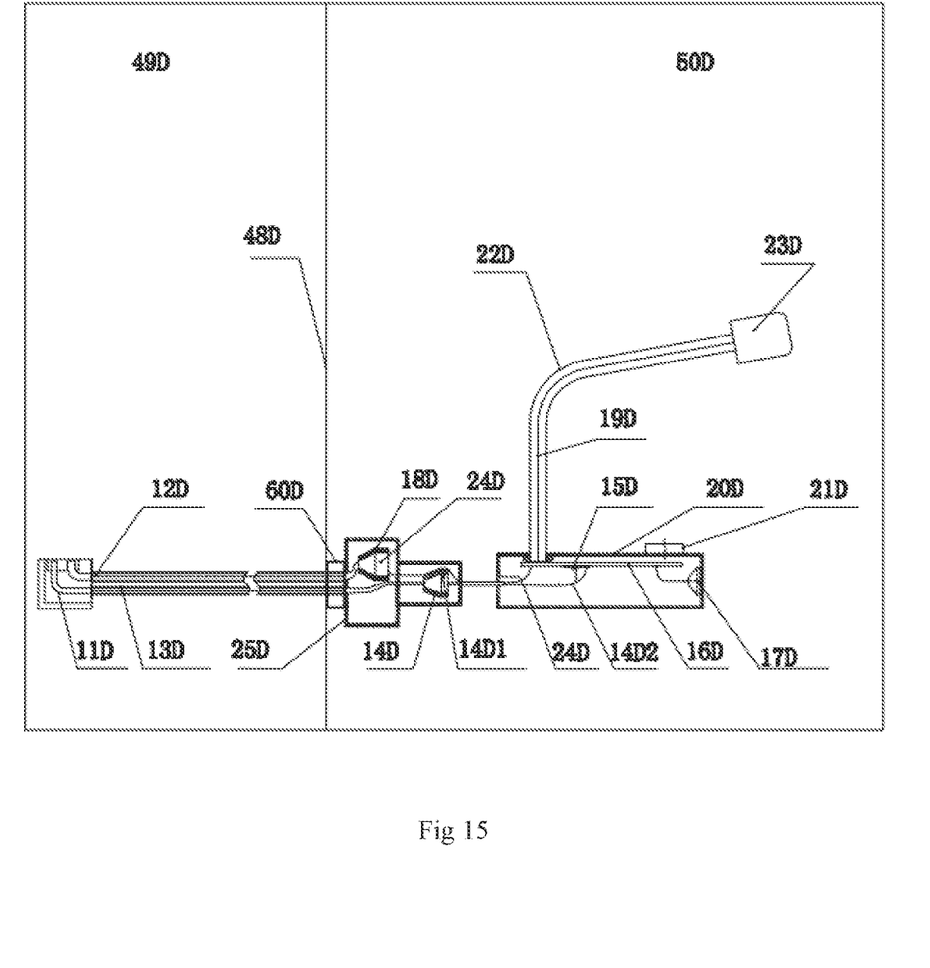
FIG. 15 is a partially schematic view of an MRI communication device provided for the embodiment 16 in the present invention.

FIG. 15 is a partially schematic view of an MRI communication device provided for the present embodiment which is a further optimization of the above embodiments. Based on the above embodiments, the Mill communication device further comprises a shielding device (60D). The control room communication module and the scan room communication module herein are the same as the ones in the above-mentioned, so they won't be repeated here.

The control room (50D) and the scan room (49D) are separated by a shield wall (48D) which has holes formed therein. The second air tube (12D) and the first air tube (13D) pass through the shield wall (48D) via the holes.

A shielding device (60D) is arranged around the holes. The second air tube (12D) and/or the first air tube (13D) are/is connected to the shielding device (60D) when pass through the shield wall (48D). As shown in FIG. 5 and FIG. 6, the shielding device (60D) has a first flange connection part (103D) and a second flange connection part (101D) joined together by screws. A mating groove having an electromagnetic shielding layer (102D) incorporated therein is disposed at one section of the second flange connection part (101D) facing the first flange connection part (103D). The first flange connection part (103D) and the second flange connection part (101D) share a centre hole and a cylinder in same sizes respectively, and the cylinders are sheathed with air tubes, which means that the first air tube or the second air tube is sleeved on the cylinders of the first flange connection part (103D) and the second flange connection part (101D). The apertures of the centre holes are identical to the inner diameters of the air tubes.

FIG. 7 and FIG. 8 are an axial cross-sectional view and a vertical view of the electromagnetic shielding layer (102D), according to which, the electromagnetic shielding layer (102D) has a plurality of through-holes formed therein. The aggregate sectional area of the holes equals or slightly larger than the inner sectional area of the air tube.

Embodiment 17

The present embodiment, a further optimization of the above embodiments, is a schematic view of the structure of the control room communication module. According to FIG. 4, the control room communication module includes a megaphone (42D), a second amplifier (44D), a second speaker (29D), a first acoustic wave concentrator (28D), an amplifier (30D), a microphone (31D), a first amplifier (45D), a first speaker (46D) and a filtering device (37D), wherein the functions of the megaphone (42D), the second amplifier (44D), the second speaker (29D), the first acoustic wave concentrator (28D), the amplifier (30D), the microphone (31D), the first amplifier (45D) and the first speaker (46D) are the same as that of the corresponding elements in the control room communication module, so it won't be repeated here. Besides, the present embodiment can set or cancel the amplifier (30D).

Figure 4:
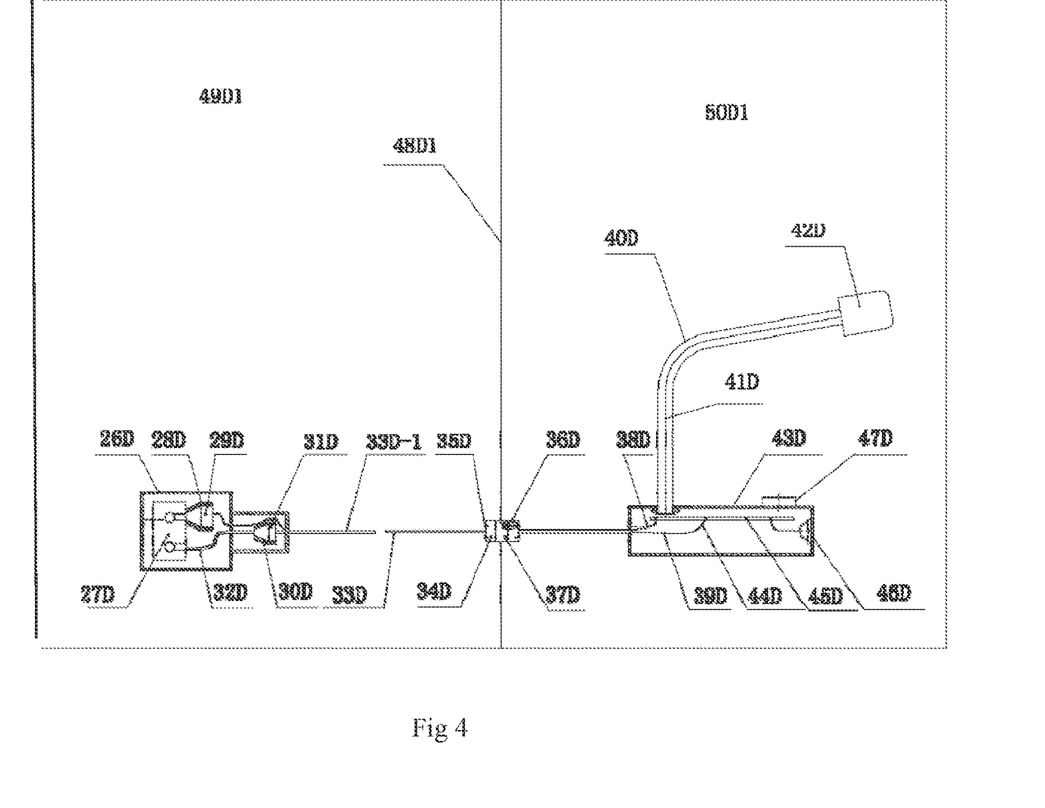
FIG. 4 is a schematic view of the arrangement of the control machine and audio signals accessed to the scan room (49D1) and the control room (50D1).

The filtering device (37D) comprises a first channel and a second channel. The second speaker (29D) connects with the second amplifier (44D) via the first channel of the filtering device (37D), and the microphone (31D) joins to the first amplifier (45D) through the second channel of the filtering device (37D). Through the function of filtering, the electrical wave signals of the first and second audio signals affecting the scan room can be filtered, reducing the effects of the communication between the control room communication module and the scan room communication module to the MRI exams.

It is notable that the above description is only preferred embodiments and technical principles. The skilled person in the field would understand that the present invention is not limited by the specific embodiments and could devise variations, rearrangements and replacements within the scope of the invention disclosed herein. Thus, although detailed descriptions are made through the above embodiments, the present invention is not intended to be limited to embodiments described herein, more other equivalent embodiments can be included without departing the spirit of the present invention, and the scope of the present invention is determined by the scope of the claims disclosed herein.

What is claimed is:

1. A MRI communication device comprising:
a control room communication module and a scan room communication module;
the scan room communication module comprises a receiver for delivering received first audio signals to a first air tube;
the control room communication module comprises a first sound device, through which the first audio signals are amplified and broadcast;
the control room communication module further comprises a second sound device, the scan room communication module further consists of an earphone, the second audio signals generated by the second sound device are transmitted to a second air tube, and then picked up by the earphone for broadcasting;
the first sound device comprises a microphone, a first amplifier and a first speaker, the first speaker, the first amplifier and the microphone are sequentially connected via wires;
the second sound device comprises a microphone, a second amplifier, a second speaker and a first acoustic wave concentrator, the first acoustic wave concentrator has a big end and a small end, the microphone, the second amplifier and the second speaker are successively connected via wires, the second speaker is disposed at the big end of the first acoustic wave concentrator, of which the small end is linked to the second air tube.

2. The MRI communication device according to claim 1, wherein the earphone includes a left-ear cover, a right-ear cover and a tee connector; a left-ear voice output port and a right-ear voice output port are respectively arranged in the left-ear cover and the right-ear cover; the tee connector comprises an input port, a first output port and a second output port; the left-ear voice output port and the right-ear voice output port respectively passes through the left-ear air tube and the right-ear air tube and connects with the first output port and the second output port of the tee connector, the input port therein is linked to the second air tube;
a receiver comprises a sound collector, a second acoustic wave concentrator, a transmission arm and a cross connector, wherein the second acoustic wave concentrator has a big end and a small end; the cross connector, including a first interface and a second interface, is disposed in the left-ear cover; the sound collector has a diaphragm configured thereon; the diaphragm is located at the big end of the second acoustic wave concentrator, and the small end, via a third air tube, joins to the first interface of the cross connector, the second interface therein is linked to the first air tube; the third air tube is disposed in the transmission arm.

3. The MRI communication device as claimed in claim 1 is characterized by the installation of a switching device between the control room communication module and the scan room communication module;
the first air tube has a first portion and a second portion, wherein the first portion is connected to the first sound device and the switching device, and the second portion joins to the switching device and the receiver;
the second air tube includes a first portion and a second portion, wherein the first portion is linked to the second sound device and the switching device, and the second portion is connected to the switching device and the earphone.

4. The MRI communication device according to claim 3, wherein the switching device has a first switching part and a second switching part used to the plug-in through connection between the first portion and the second portion of the first air tube and/or between the first portion and the second portion of the second air tube.

5. The MRI communication device according to claim 4, wherein the first switching part includes a first hole core and a second hole core, while the second switching part consists of a first jack and a second jack;
the first portion of the first air tube and the second air tube are respectively connected to the first hole core and the second hole core, and the second portion of the first air tube and the second air tube join to the first jack and the second jack respectively;

when the first switching part is connected to the second switching part, the first hole core and the second hole core through-connect with the first jack and the second jack respectively.

6. The MRI communication device as claimed in claim 1 is characterized in that the longer the first air tube or the second air tube is, the larger the diameter is.

7. The MRI communication device according to claim 1, wherein the control room communication module and the scan room communication module are respectively disposed in the control room and the scan room of a MRI exams, the control room and the scan room are separated by a shield wall, which has holes formed thereon to provide a passageway to the first air tube and the second air tube;

a shield device is arranged around the holes, the shielding device has a first flange connection part and a second flange connection part joined together by screws, a mating groove having an electromagnetic shielding layer incorporated therein is disposed at one section of the second flange connection part facing the first flange connection part, the first flange connection part and the second flange connection part share a centre hole and a cylinder in same sizes respectively, and the cylinders are sheathed with air tubes, the apertures of the centre holes are identical to the inner diameters of the air tubes.

8. The MRI communication device according to claim 1, wherein the control room communication module further includes a filtering device having a first channel and a second channel, the second speaker connects with the second amplifier via the first channel of the filtering device, and the microphone joins to the first amplifier through the second channel of the filtering device.

* * * * *